United States Patent [19]

Storm, III

[11] 4,140,130
[45] Feb. 20, 1979

[54] ELECTRODE STRUCTURE FOR RADIO FREQUENCY LOCALIZED HEATING OF TUMOR BEARING TISSUE

[76] Inventor: Frederick K. Storm, III, 11400 Albata St., Los Angeles, Calif. 90049

[21] Appl. No.: 802,273

[22] Filed: May 31, 1977

[51] Int. Cl.$^2$ .............................................. A61N 1/40
[52] U.S. Cl. ................................... 128/404; 128/400; 128/413; 128/416; 128/422
[58] Field of Search ............... 128/404, 405, 406, 407, 128/408, 409, 410, 411, 413, 416–418, 422, 24 A, 399, 400, 401

[56] References Cited

U.S. PATENT DOCUMENTS

| 1,531,414 | 3/1925 | Ruben | 128/399 |
| 1,849,745 | 3/1932 | Hoffman | 128/416 X |
| 2,220,269 | 11/1940 | Patzold et al. | 128/413 |
| 3,045,100 | 7/1962 | Mills | 128/399 X |
| 3,237,623 | 3/1966 | Gordon | 128/24 A |
| 3,307,553 | 3/1967 | Liebner | 128/400 |
| 3,991,770 | 11/1976 | LeVeen | 128/413 |
| 4,026,290 | 5/1977 | Sauder | 128/400 |

FOREIGN PATENT DOCUMENTS

| 557950 | 5/1958 | Canada | 128/416 |
| 2407559 | 8/1975 | Fed. Rep. of Germany | 128/404 |
| 1086062 | 2/1955 | France | 128/404 |

OTHER PUBLICATIONS

LeVeen et al., "Tumor Eradication ... Therapy", JAMA, May 17, 1976, vol. 235, No. 20, pp. 2198–2200.
Lehmann et al., "Evaluation of a Microwave ... Applicator", Arch. of Phys. Med. & Rehab., Mar. 1970, pp. 143–146.
DeLateur et al., "Muscle Heating ... Applicator", Arch. of Phys. Med. & Rehab., Mar. 1970, pp. 147–151.
Doss et al., "A Technique for Localized Heating in Tissue ...", Med. Inst., vol. 10, No. 1, Jan. 14 Feb. 1976, pp. 16–21.

Primary Examiner—Lee S. Cohen
Attorney, Agent, or Firm—Poms, Smith, Lande & Glenny

[57] ABSTRACT

An electrode structure for use in emitting electromagnetic radiation for localized heating of tissue in medical therapy and capable of permitting deep heat penetration while skin surfaces and subcutaneous tissue remain at lower and physiologic temperatures not harmful to living tissue. An electrode structure having a wall with an emitting surface adapted to be placed in direct facial contact or in close proximity with external skin surfaces, the wall forming part of a cooling chamber through which cooling fluid is circulated to maintain the wall and adjacent tissue at selected relatively cool temperature. The electrode wall is connected to a radio frequency generator through impedance matching circuitry. In one embodiment, the wall surface is suitably curved for direct uniform contact with the surface configuration of the body to which it is applied. In another example, one wall is made of a flexible, metallized material to serve as an electrode and to provide a surface closely conforming to external surface configuration of such body. In a further embodiment, the entire electrode is flexible — the cooling chamber and metallized material both closely conform to external surface configuration of such body. In all examples, extended area cooling may be provided by additional or auxiliary cooling chamber peripheral to, and beyond, the electrode surface.

16 Claims, 18 Drawing Figures

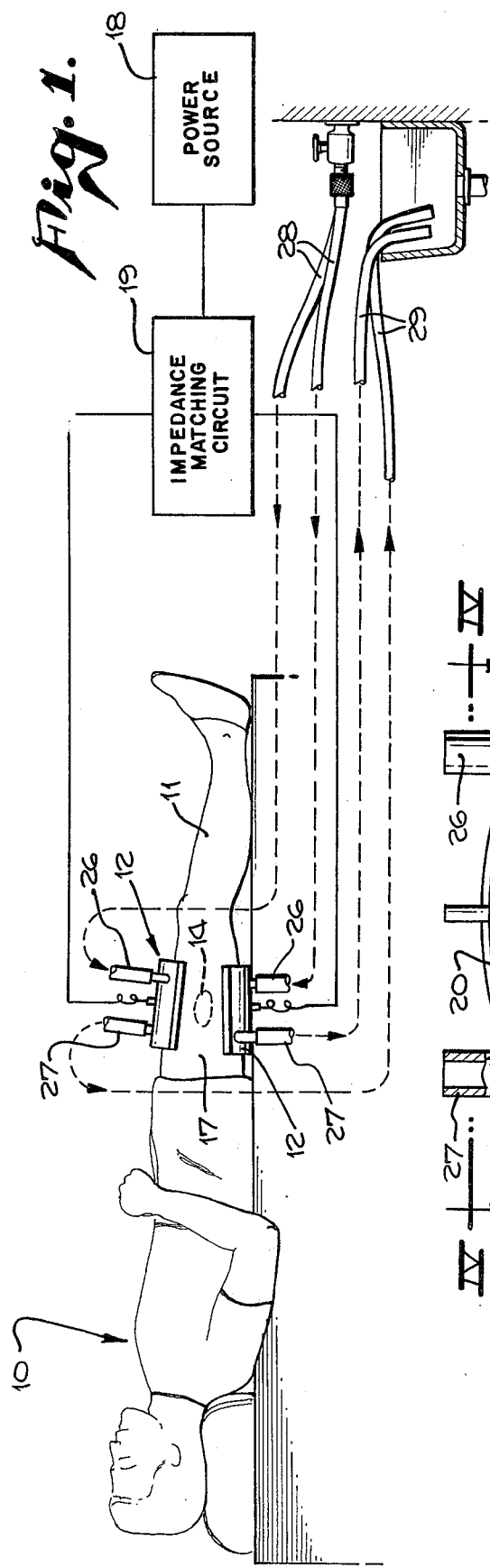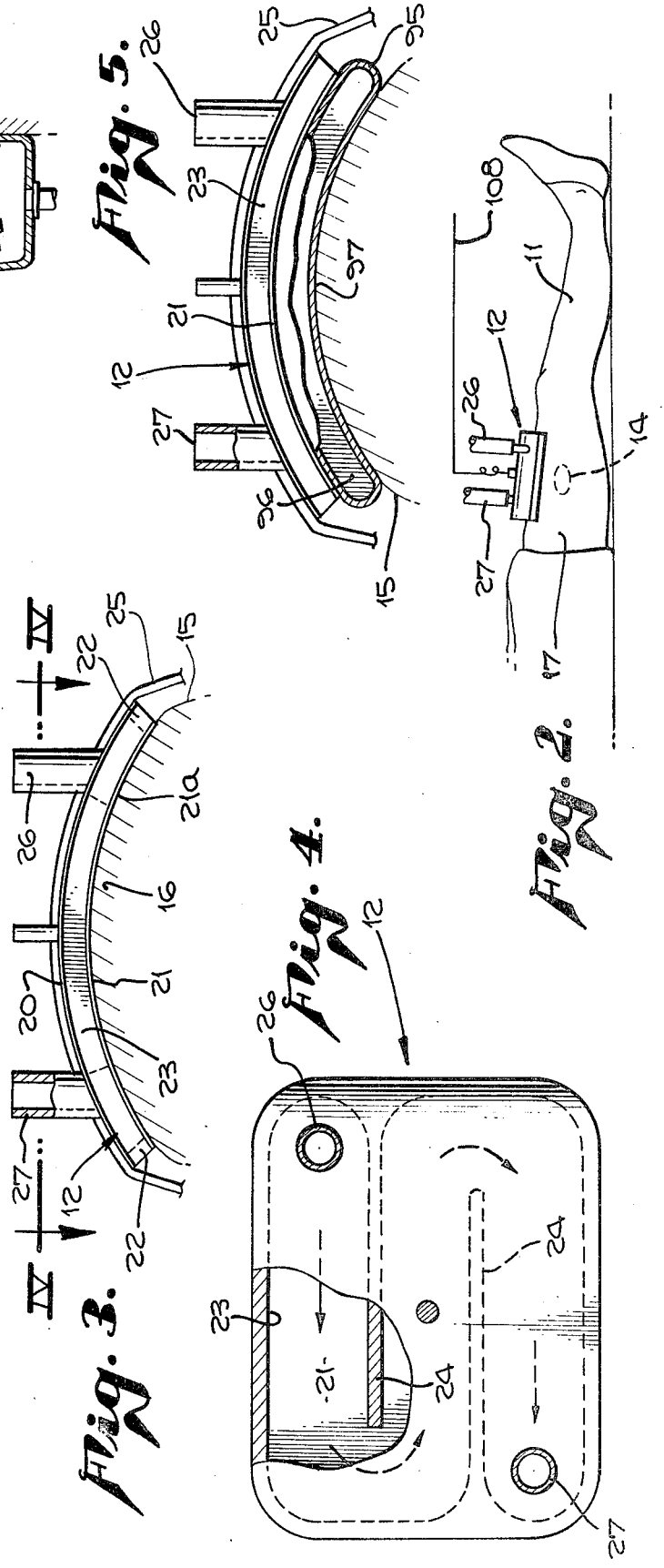

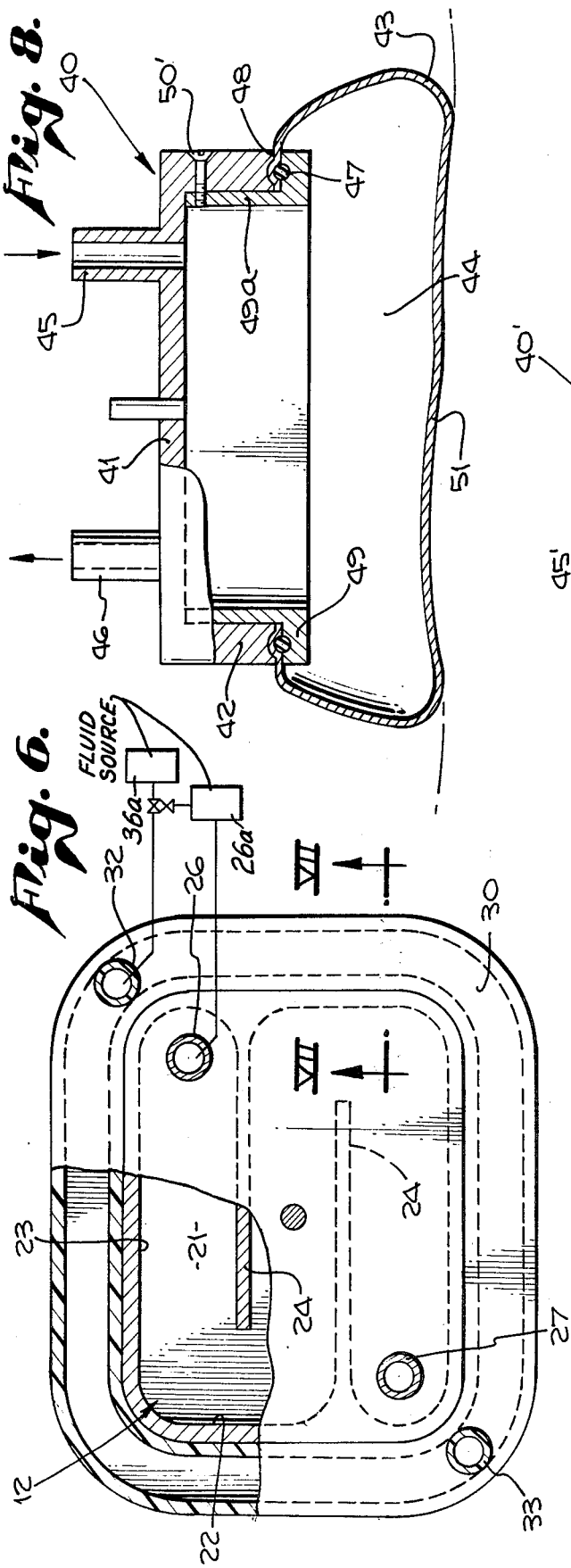
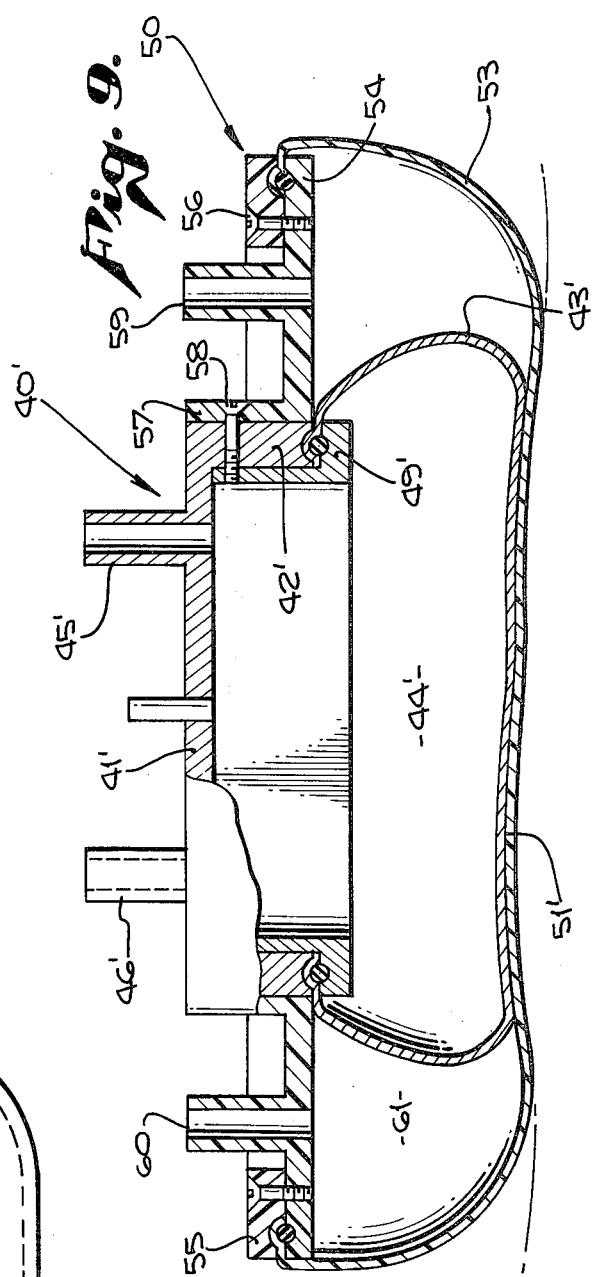
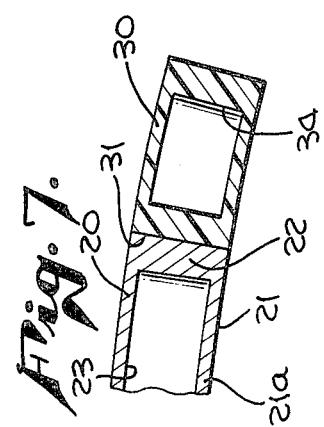

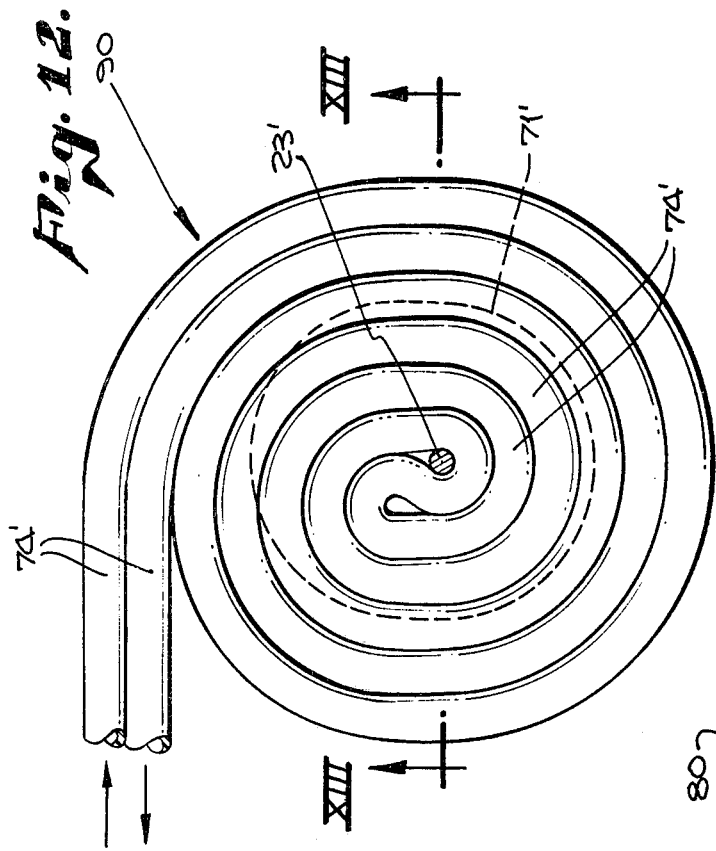
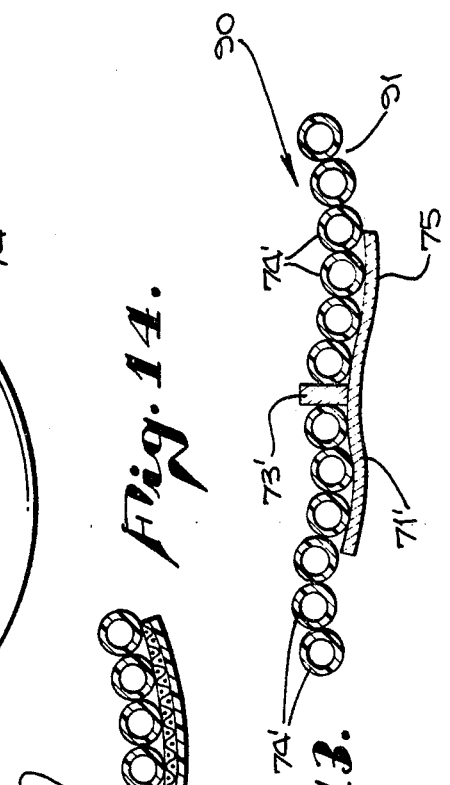
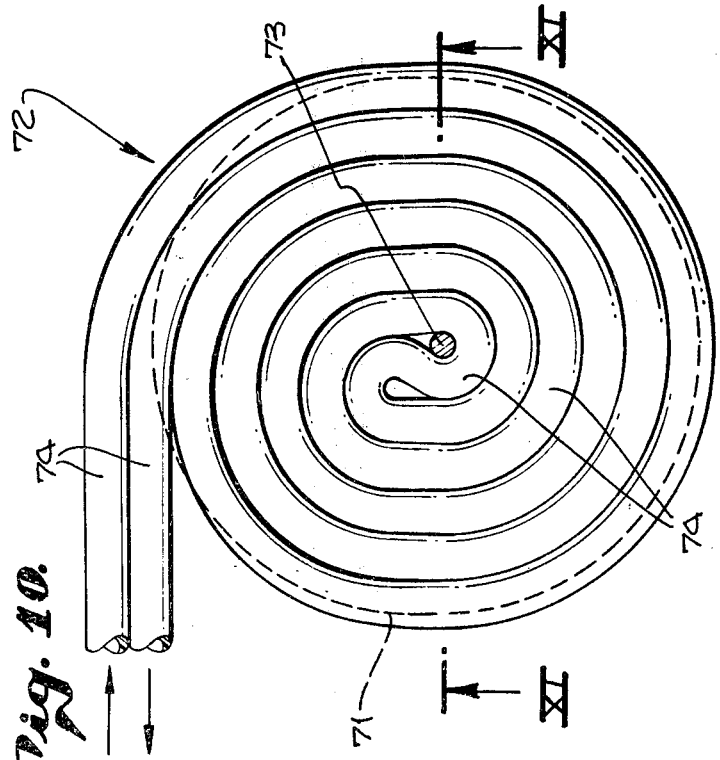
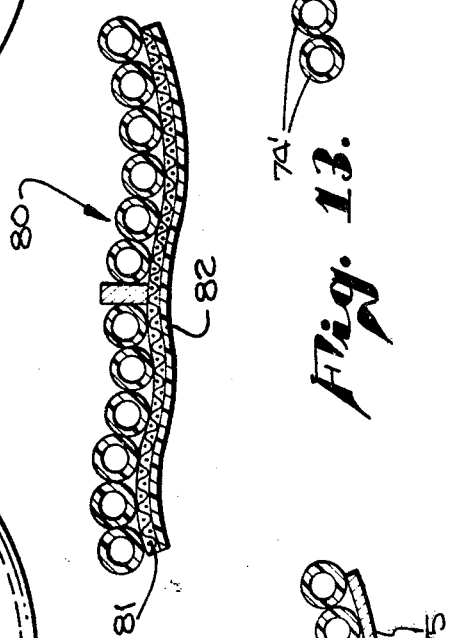
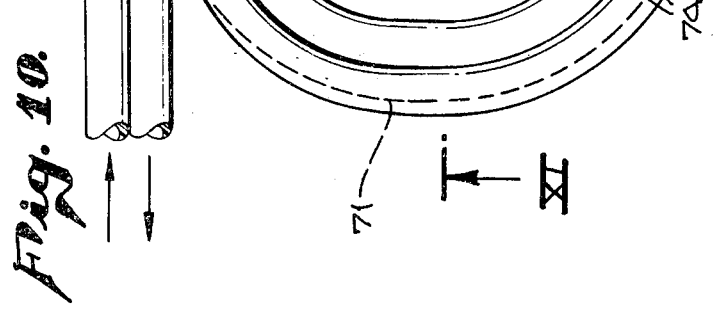
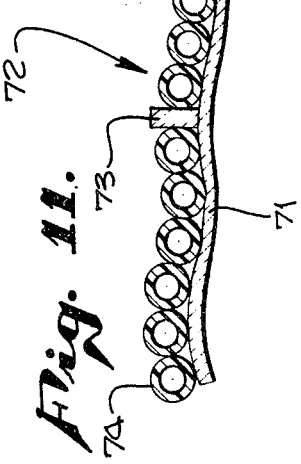

HUMAN TUMOR : 15 X 15 X 15 c.m.

ELECTRODE STRUCTURE FOR RADIO FREQUENCY LOCALIZED HEATING OF TUMOR BEARING TISSUE

BACKGROUND OF THE INVENTION

Extensive research has been conducted on the unique characteristics of tumor bearing tissue and the treatment thereof by various techniques. One discovered characteristic of tumor bearing tissue is that blood flow through the tumor is substantially less; for example, 2% to 15%, than blood flow through surrounding normal tissue (Radio Frequency Therapy JAMA 5/17/76, Volume 235, No. 20, LeVeen et al). Because of this vascularity of tumor tissue, under heat therapy such tumor tissue acted as a heat reservoir, was unable to dissipate heat at the same rate as surrounding normal tissue, and therefore reached temperatures from 5° C. to 10° C. higher than normal tissue under certain treatment procedures. Such temperature differential suggested bringing tumorous tissue to temperatures in the range of 45° C. to 50° C., at which the tumorous tissue would be destroyed or subject to substantial regression, with preservation of normal tissue at physiologic temperatures. Substantial regression of the tumorous tissue may be a beneficial adjunct to other forms of treatment of tumors, such as surgery, radiation, chemotherapy, and immunotherapy.

Medical diathermy, used for decades in musculo-skeletal disorders, has limitations to deep heating imposed by the inability to provide for surface tissue protection by cooling. Provision of surface tissue at physiologic temperatures, while causing deep musculo-skeletal heating, would broaden the applications for medical diathermy in varied disease states (sprains, strains, arthritis, etc.).

Various ways of heating body tissue have been proposed. Localized application of heat by use of electromagnetic energy derived from radio frequency generators has been conducted in the ranges of ultrasonic frequencies 0.8–1.0 MHz, shortwave frequencies 13–27 MHz and microwave frequencies 915–2450 MHz. Most relevant to (but not a limitation of) the present invention is the shortwave frequency, which is described in said publication on Radio Frequency Therapy. Shortwave generates less heat in fat with deep penetration and is the longest band width (13.56 MHz) approved by the Federal Communications Commission for medical use.

One of the problems encountered in localized application of radio frequency waves to tissue is that of severe burning of skin and subcutaneous tissues. Surface cooling in a microwave field at 915 MHz has been proposed by using a microwave antenna in non-surface contact with the skin and blowing cooled air onto the skin through the space between the radio frequency emitter and the skin. Another cooling method is described in application of heat to muscle in human subjects with a 915 MHz microwave contact applicator in which coolant was circulated through a dielectric cooling plate of a microwave applicator in which the emitter was an antenna in a tuned cavity type applicator, the emitter antenna being relatively widely spaced from the dielectric cooling contact plate. (*Archives of Physical Medicine and Rehabilitation,* March 1970, pages 143–151, "Evaluation of a Microwave Contact Applicator," Lehman et al and "Muscle Heating in Human Subjects With 915 MHz Microwave Contact Applicator," LeLateur et al.)

SUMMARY OF THE INVENTION

The present invention relates to a novel electrode means for use in the localized application of heat to tissue without damage to living tissue. The invention contemplates an electrode means so constructed and operable to provide deep heating, where necessary, by emitting shortwave or microwave frequencies to establish an electromagnetic field with the tumor bearing tissue therein and to provide adequate cooling of skin and subcutaneous tissues surrounding the tumor bearing tissue, or to establish an electromagnetic field to provide for deep heating in musculoskeletal disease states or conditions.

This invention particularly contemplates an electrode means for interfacial contact or close proximity with the skin surface of a body having a cancerous tumor wherein a shortwave radio frequency is generated in the nature of 13.56 MHz, and wherein the electromagnetic field is generated between two opposed electrodes embodying this invention disposed on opposite sides of the body with the tumor bearing tissue therebetween. An impedance matching circuit is connected with the electrode means and the radio frequency generator so that the impedance of the body portion lying between the electrodes and the impedance of the generator may be suitably matched. An electrode acting as a microwave antenna could impart a directional electromagnetic field from a single electrode directed at the body part. Each electrode means is provided with a chamber through which cooling fluid is circulated at a selected rate of flow to maintain the wall of the chamber in contact with the skin of the patient at a selected temperature. The proximity and, sometimes preferred, direct contact of the electrode wall with the skin surface minimizes possible changes in the impedance of the body portion caused by changes in the electromagnetic field and also acts as a heat transfer means for maintaining the skin and subcutaneous tissue therebeneath in a suitably relatively cooled state while a selected dosage of heat is being applied to tumor bearing or deep musculo-skeletal tissue. The invention contemplates that the wall of the electrode means may be suitably configured to closely fit to the contour configuration of the body member against which it is placed.

In another example of the electrode means, one wall is made of a flexible compliant metallized conductive material so that the wall may be readily adjusted to the surface configuration of the body member under pressure of the circulating cooling fluid. When the electrode means includes a relatively non-compliant, thin section metal wall, the electrode means may be pressed against the surface of the body member to conform the skin to the configuration of the electrode wall.

In a further example, virtually all portions of the electrode means are flexible, cooling being provided by a spiral of flexible tubing in which coolant is circulated and which overlays flexible metallized material. Both tubing and flexible material make close surface contact and conform and yield to body surface contour.

To increase surface contact on very irregular skin surfaces, another example of the invention contemplates use of a thin flexible pliant bag filled with electrolyte solution and placed between the surface and an electrode means of this invention. The electrolyte solution then becomes an effective extension of the electrode means and itself emits electromagnetic waves. The thin bag filled with static electrolyte solution is cooled by contact with the electrode means.

In all examples, means are provided for a second and peripheral cooling chamber of non-metallic material to provide for surface cooling of tissue peripherally adjacent to, but not contacted by, the electrode emitting surface. This provides cooling of adjacent peripheral tissue heated by the near electrode field which spreads peripherally outwardly from the emitting electrode edge.

The primary object of the present invention therefore is to provide a novel electrode means for localized application of heat by electromagnetic energy to tumor bearing and deep musculo-skeletal tissue.

An object of the present invention is to provide an electrode means adapted to be secured in direct interfacial contact with the surface of the body being treated to minimize changes in impedance between the electrode means.

Another object of the invention is to provide a novel electrode means including cooling means for control of tissue temperature in the electromagnetic field.

A further object of the present invention is to provide an electrode means having a surface for direct uniform contact with the surface of the skin of a body and wherein the surfaces in contact are substantially conformed one to the other.

A still further object of the present invention is to provide an electrode means wherein a cooling chamber is formed, and cooling fluid is circulated through the cooling chamber or tubing to provide transfer of heat through a wall of the chamber to adjacent tissue of a body for maintaining a selected temperature of said adjacent tissue during localized heating of an internal tumor bearing tissue or the treatment of musculo-skeletal disease conditions.

Still another object of the present invention is to provide an electrode means having a flexible electrode wall or a completely flexible electrode means readily conformable to the configuration of the surface of skin of a patient to which the electrode is applied.

Still another object of the invention is to provide an electrode means having a flexible electrode wall as mentioned above wherein said wall forms part of a cooling chamber and wherein cooling fluid in said chamber imposes fluid pressure on said wall to conform said wall to the configuration of the skin surface of the patient.

Still another object of the invention is to provide for means of cooling tissue adjacent to the electrode, not contacted by the electrode but subjected to heating by the effects of the near electromagnetic field.

A general object of the invention is to provide a novel electrode means including circulating cooling means whereby the skin and subcutaneous tissue of a body are preferentially cooled in the presence of heating effect of coincident radio frequency waves while said radio frequency waves heat tumor bearing tissue to a sufficient temperature to cause necrosis or regression of the tumor tissue, or heat deep musculo-skeletal tissue for its theraputic benefit in disease states or conditions.

The invention further contemplates electromagnetic heating of tissue at relatively great depths with control of superficial heating of living tissue and for the non-invasive treatment of relatively deeply located tumor or otherwise diseased tissue.

The invention specifically contemplates an electrode construction for transmitting electromagnetic energy and adapted to be connected to a power source in which the electrode construction includes an electrode body having an emitting surface adapted to be placed in at least close proximity, if not direct contact, with a surface of a body being treated and means for cooling the emitting surface and adjacent body surfaces. The cooling means includes means for circulating cooling fluid in heat transfer relation to the emitting surface and to the body surface.

The invention further contemplates another embodiment wherein a flexible emitting surface is contained within a flexible bag having inlet and outlet fittings for cooling fluid and also containing porous flexible material within the bag to position and hold the flexible emitting surface in contact with the wall of the bag positionable against a skin surface.

Many and other objects and advantages of the present invention will be readily apparent from the following description in which the drawings illustrate exemplary embodiments of an electrode means of this invention.

IN THE DRAWINGS

FIG. 1 is a schematic view of a patient having electrode means of this invention applied to his body, the electrode means being schematically connected to an impedance matching circuit and power source for emitting radio frequency waves through the electrode means to create an electromagnetic field between the electrode means, and also being connected to a controllable cooling means.

FIG. 2 is a fragmentary schematic view similar to FIG. 1 showing an electrode means of this invention used to emit waves of microwave frequency for particular use in muscular skeletal heating.

FIG. 3 is an end view of an electrode means shown in FIG. 1, the view partly in section and fragmentarily showing strap securing means.

FIG. 4 is a top view of FIG. 3 taken in the plane indicated by FIG. IV—IV of FIG. 3, the view being partly in section to show circulation of cooling fluid through the electrode means.

FIG. 5 is an end view similar to FIG. 3 of an electrode means of the invention as shown in FIGS. 3 and 4 used with a separate bag containing electrolyte solution.

FIG. 6 is a top plan view similar to FIG. 4 showing a modification of the electrode means of the invention shown in FIGS. 3 and 4.

FIG. 7 is a fragmentary enlarged vertical sectional view taken in the plane indicated by line VII—VII of FIG. 6.

FIG. 8 is a vertical sectional view of an electrode means embodying a modification of the invention showing a flexible wall and flexible emitting surface.

FIG. 9 is a sectional view similar to FIG. 8 and shows a modification of the invention in which two flexible walls define inner and outer separate cooling chambers, the emitting surface being on the wall of the inner chamber.

FIG. 10 is a top plan view of a still further modification of the electrode means of this invention embodying a spiral tube for cooling fluid.

FIG. 11 is a vertical transverse sectional view of FIG. 10, the section being taken in the plane indicated by line XI—XI of FIG. 10.

FIG. 12 is a top plan view of an electrode means embodying a still further modification of this invention in which additional outer turns of tubing providing cooling fluid are provided.

FIG. 13 is a sectional view taken in the vertical transverse plane indicated by line XIII—XIII of FIG. 12.

FIG. 14 is a sectional view similar to FIGS. 11 and 13 and illustrates a further modification of the flexible wall of the emitting surface, in this example a flexible screen.

Figure 17:
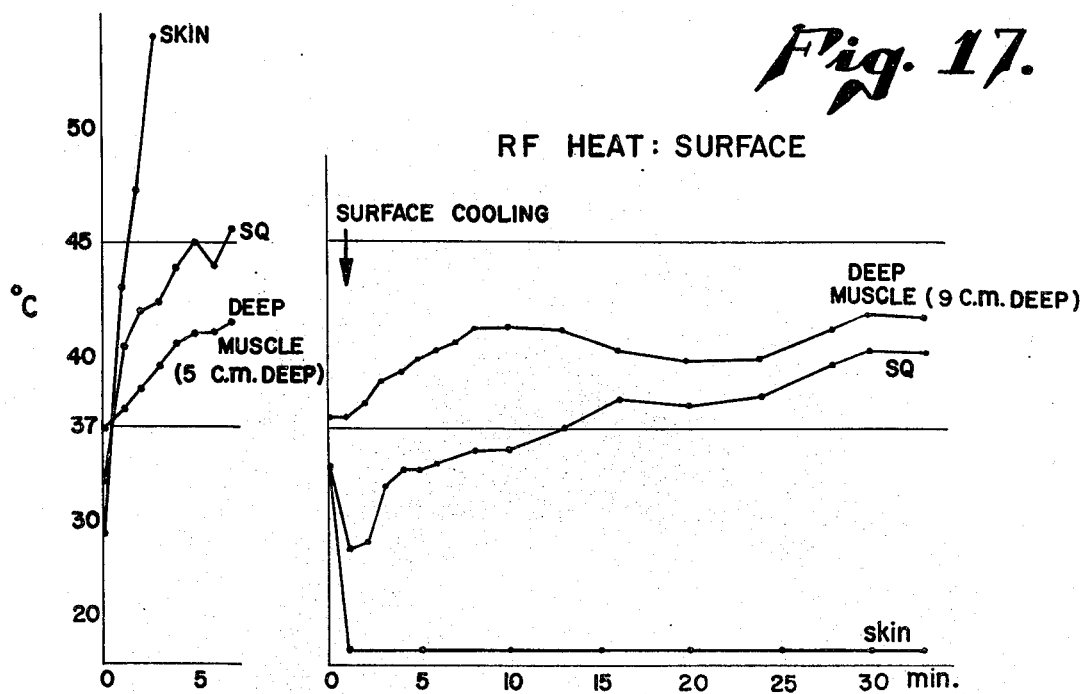

FIG. 17 discloses two charts showing the effect of electrode heating with and without surface cooling means, the chart at the left being without cooling means and the chart at the right being with surface cooling means.

Figure 18:
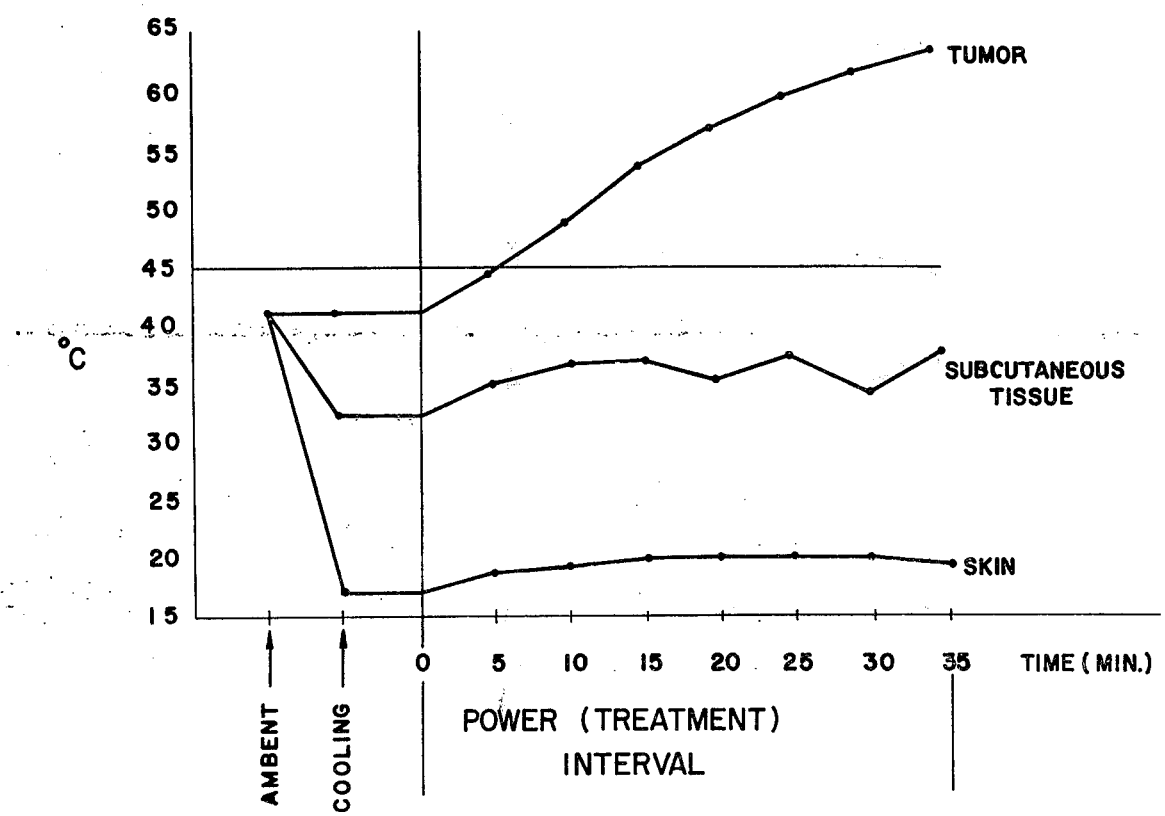

FIG. 18 is a chart illustrating internal heating of a human tumor while maintaining skin and subcutaneous tissue at substantially cooler temperatures.

Referring generally to FIG. 1, a patient is illustrated having a body 10 with a leg 11 to which is externally applied electrode means 12 embodying this invention. In the illustration, it is assumed that the thigh of leg 11 has an internal body portion, indicated in dotted lines 14, which comprises tumor bearing tissue or diseased musculo-skeletal tissue. Surrounding body portions of non-tumor bearing tissue or normal tissue include subcutaneous tissue 16 (FIG. 3) and skin 15 having external skin surfaces. As noted hereinabove, blood flow within tumor bearing tissue 14 is substantially less than blood flow through surrounding normal tissue 17. The effect of heating normal tissue increases blood flow through normal tissue and protects against the effects of the heat. Blood flow is substantially less in the tumor bearing tissue 14 which acts as a heat reservoir and therefore the temperature of the tumor bearing tissue will more rapidly rise than that of the surrounding normal tissue. This characteristic of tumor bearing tissue is fully described in the article by H. H. Leveen, "Journal of the American Medical Association" 235; 2198, 1976, noted above. LeVeen found that tumor blood flow under heat conditions was only 2–15% that of surrounding tissue. In musculo-skeletal disease states, the direct effect of deep heat on diseased tissue may augment healing.

The tolerance of normal tissue (fat, muscle, skin) to heat depends upon the amount of heat, the time during which the tissue is subjected to heat, as well as the amount of power used to generate the radio frequency.

In the apparatus of the present invention, a power source 18 may comprise a suitable known shortwave or microwave transmitter or generator capable of emitting radio frequencies in the order of 13.56 Mhz to 2450 MHz and having a power rating of up to 3 kilowatts. Power source 18 is suitably electrically connected to the electrodes 12 through electrical circuitry which includes an impedance matching circuit 19 in order to precisely and closely match the impedance of the material of the body portion between the electrodes with the generator. The conductivity of the material of the body portions will vary depending upon whether such body materials have high or low water content, and the amount of skin, muscle or fat which are in the body portions. For example, Geddes and Baker (*Medical and Biology*, Volume 5, pages 271-293, 1967) describes the following conductivity or resistance of materials comprising human skin to be 289 ohms per centimeter, and human fat to be in the range of 2000 to 5000 ohms per centimeter.

In the example of electrode means 12 shown in FIGS. 1, 3, 4 electrode means 12 comprises a top wall 20, a bottom wall 21 and side or edge walls 22 which extend peripherally around the electrode means. The walls may be made of thin metal having characteristics of effective and efficient transfer of heat and also electrical conductivity. Examples of thin metal having such characteristics are phosphor bronze and beryllium copper, which may be obtained in wall thicknesses of from 0.005 to 0.25 inches. Such walls of thin metal may be readily formed in a curved shape for general correspondence with the configuration of the external surface of a body with which the bottom wall 21 may be placed in contact.

The top, bottom and side walls form a hollow chamber for circulation of cooling fluid. The spacing of the top and bottom walls may be 0.25 inches. The spacing may be more or less depending upon the design criteria for the electrodes and its specific use.

Bottom wall 21 has a surface generally contoured to the skin surface to provide uniform interfacial direct contact with the skin surface 15 over the entire surface area of wall 21. The surface area of wall 21 may vary between 50–500 square centimeters and it is understood that such surface area variation will also depend upon the configuration of the body portion and external skin surface to which the electrode means is directly applied. Direct skin contact by securing electrodes 12 on opposite sides of the internal body portion 14 to be treated with a non-conductive strap 25 applied over the electrodes. Such non-conductive or dielectric strap is fragmentarily shown in FIG. 2 and not only secures the electrodes in fixed position on the body, but also may be sufficiently tightened to press the bottom walls 21 of the electrode means into intimate direct contact with the skin surface 15 and to cause uniform contact of the entire surface area of wall 21 with the skin. Such fixed, uniform contact of a predetermined area of bottom wall 21 with the skin surface is of importance in maintaining balanced electromagnetic fields at each electrode as later described.

Means for uniform cooling of the electrode means 12 includes suitably arranged partitions 24 in chamber 23 to cause cooling fluid to circulate in heat transfer relation with the bottom wall 21 of the electrode means 12. The cooling means includes an inlet fitting 26 and an outlet fitting 27 which are adapted to be connected to suitable tubes or conduits 28 and 29 for conducting and circulating cooling fluid into and out of the electrode means 12. The inlet fitting 26 may be connected to a water line readily available in hospitals, clinics and elsewhere, or to a suitable closed circuit refrigeration unit to provide selected cooling, for example, (0° C.) as required. The discharge outlet 27 and conduit 29 may be connected to a suitable drain or to a suitable reservoir for conserving water circulated through the electrodes. It will also be understood that the cooling fluid may be provided by any suitably cooling fluid supply source at a preselected temperature and may be circulated by a suitable pump means (not shown) for causing sufficient flow of the cooling fluid to produce the desired cooling effect on the body portions. The selected rate of flow of cooling fluid will depend upon the temperature of the cooling fluid available, on the desired temperature of the skin and subcutaneous tissue, the depth of penetration of the heat applied to the internal body portions by the radio frequency waves, and the length of time of the treatment.

Control of the circulation of the cooling fluid may also be dependent upon the observation of precisely located needle-type thermometers placed in the body at critical locations and depth to determine internal temperatures of the normal tissue and tumor bearing tissues. Such needle-type thermometers may be of any suitable manufacture and are accurate to 0.1° C. and may be applied by using standard medical catheters.

The cooling fluid has been exemplified above as being tap water. For precise control and under certain circumstances, it may be desirable to use other types of liquid or gas which would permit effective efficient regulation of the transfer of heat from the skin surfaces and subcutaneous tissue to the cooling fluid through the bottom wall 21 of the electrode means. The type of cooling fluid used may also depend upon the length of time of the treatment, to the amount of power used during treatment, and to the surface temperature required.

The circuitry illustrated in FIG. 1 is exemplary only since the impedance matching circuit may be a conventional circuit. It is important to note that the impedance of the material of the body portions between the electrodes 12 may be determined and matched by placing the electrode means on the skin surfaces in opposed relation with the tumor bearing tissue therebetween and applying a suitable minimum amount of power; for example, 50 watts to the circuit. A pair of directional power meters are employed in the circuit, one of which reads the reflected power and the other of which reads the incident power. The circuit includes means for adjusting the circuit to minimize reflection and then to further adjust the circuit to bring it into a resonance condition. It is important that the electromagnetic field for each electrode means 12 should be equalized and such fields are measured and adjusted to provide the desired balance. It will thus be apparent that while the impedance matching circuitry may be conventional, the direct interfacial contact between the skin 15 and the surface of bottom wall 21 remains unchanged during treatment and therefore the physical conditions minimize chances of unbalancing of the matched impedances which might create a condition causing burning of the skin surface or unwarranted heating of subcutaneous tissue.

Similar advantages of a cooled, surface electrode would apply to microwave frequencies, where a single electrode means 12a (FIG. 2) might be used as a microwave antenna. In such use the power generator, impedance matching circuit, and other parts would be modified and changed for the effective emission of microwaves.

In treatment of a tumor bearing tissue such as internal body portions 14, the location of the tumor bearing or otherwise diseased tissue is determined by known procedures. Electrode means 12 are placed on opposite side of the internal body portion 14 and the circuitry is placed in balance as above described so that the material of the body portions between the electrode means and its impedance is balanced with the impedance of the generator and the electrical fields at the electrodes are in balance. When the radio frequency waves are generated by the power source and transmitted by the electrode means 12 into the body portions between the electrode means, internal heating of the body portions will occur in a manner similar to well-known diathermy, shortwave and microwave processes. The amount of power used in such treatment depends upon the emitting area of the electrode means and the power of the generator. Heating of the tumor bearing or otherwise diseased tissue and the normal tissue surrounding the tumor bearing tissue is monitored by the use of a plurality of needle-like thermometers, as above-described. The cooling fluid is controlled so that sufficient flow of cooling fluid is provided through the chambers of the electode means 12 to maintain the skin and subcutaneous tissue at selected temperatures. The length of application of shortwaves to the tumor bearing or otherwise diseased tissue and the dosage thereof may be selected in accordance with the specific conditions of the patient.

It will be understood that the construction of electrode means 12, as described above, together with the control of cooling fluid and the use of a 3 kilowatt generator or a generator of selected power, provides deep penetration with heat, up to 9 centimeters, such as internal body portion 14, while maintaining the skin surface and subcutaneous tissue at a substantially lower temperature to prevent damage thereto or burning of the skin surfaces.

Figure 15:
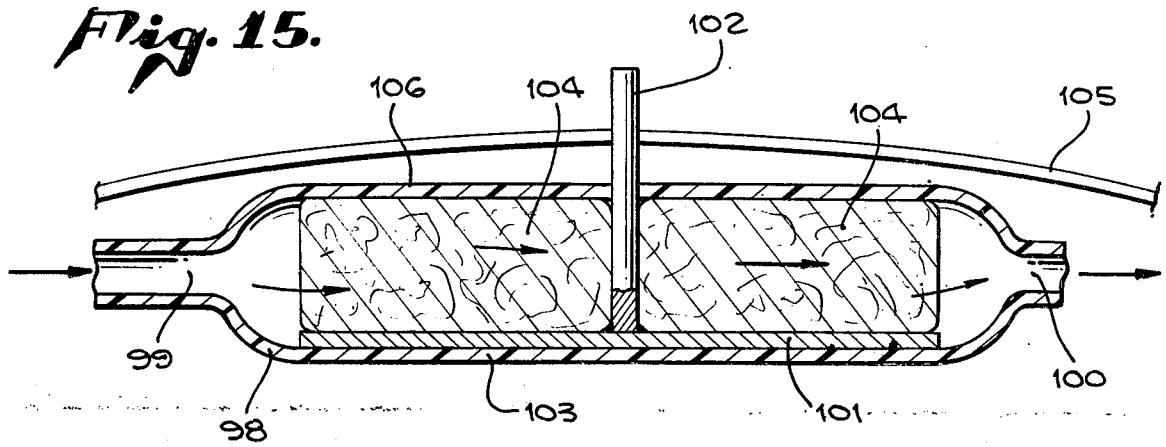
FIG. 15 is a vertical transverse sectional view of another embodiment of this invention in which the emitting surface is contained within a flexible bag through which cooling fluid is circulated.

Experiments on animals and humans have been conducted and an example of such temperature differential using the electrode means of this invention is illustrated in the chart of FIG. 15. The chart illustrated on FIG. 15 was evolved from treatment of a lung tumor in a dog by electrode means and apparatus embodying the present invention as described above. It is known and it will be understood that tests have indicated that certain portions of the body protectively adapt themselves to heat more than other portions of the body, such portions being in the case of an animal, such as a dog, the heart, lung and liver.

Figure 16:
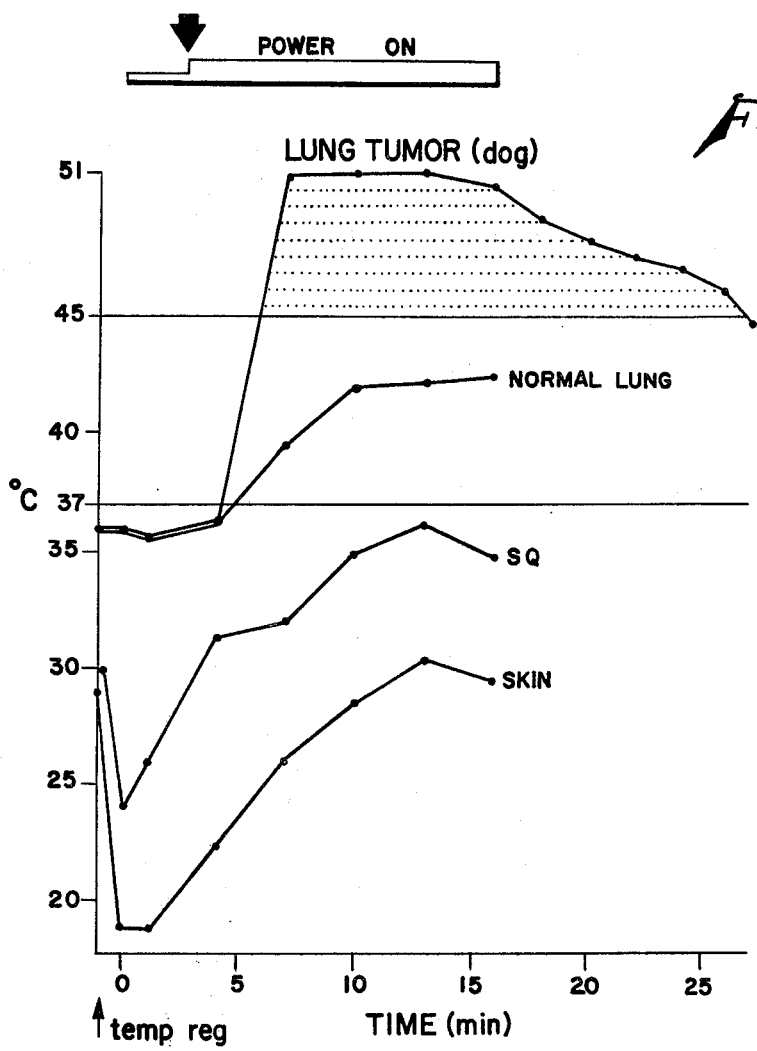
FIG. 16 is a chart illustrating internal heating of an animal lung tumor while maintaining skin and subcutaneous tissue at substantially cooler temperatures, the chart being illustrative of heating and cooling effects obtained by electrode means of this invention.

With reference to the chart shown in FIG. 16, the temperature in degrees centigrade is shown on the Y axis, and the time of dosage or treatment on the X axis. Before treatment it will be noted that the temperature of the skin is about 29° C., that of the subcutaneous tissue about 30° C., and that of the lung, including lung tumor, about 36° C. Upon commencing treatment, which begins with the circulation of the cooling fluid, the temperature of the skin and subcutaneous tissue dropped to 20° C. and 24° C., respectively, as a result of the circulation of the cooling fluid. After one minute, the generator was started with only partial power and for the next three minutes the temperature of the skin and the subcutaneous tissue increased as shown on the chart. At four minutes additional power was introduced whereby the temperature of the lung and lung tumor increased substantially. It should be noted that after seven minutes the lung tumor reached 51° C. and maintained this temperature until 13 minutes had elapsed and then for the next three minutes while power was on, only decreased by a half a degree centigrade. Power was turned off at 16 minutes, and from that point on the temperature of the lung tumor decreased as shown on the chart. The area of the chart sectioned under the line illustrating the temperature and time during which the temperature is sufficiently high to destroy the cancerous tissue. The chart also indicates that the lung reaches a temperature of only 42.5° C., at which temperature the lung can survive because of its protective heat adaptive characteristic. Of significant importance is the cooling effect of the cooling fluid on the skin and subcutaneous tissue in which the subcutaneous tissue reaches a top temperature of only 36° C. and the skin of only 30.5° C., both of which temperatures are substantially below temperatures at which normal living tissue would be damaged or destroyed. It will be understood that the illustration of FIG. 16 shows the results of the application of the electrode means of this invention on an animal; that is, a dog, in order to illustrate the temperature results achieved by the electrode means of the present invention.

The two charts of FIG. 17 compare the degree of surface temperature comprised of skin and subcutaneous tissue with the degree of deep muscle heating, without and with surface cooling provided. The small chart at the left of FIG. 17 shows that without surface cooling the skin reaches an injurious level of surface heat indicated as well over 50° C. The subcutaneous tissue reaches an injurious level of heat of about 45° C. Meanwhile, the deep muscle portion of the body at 5 centimeters depth shows heating only to about 41°, 42° C.

In the chart on the right part of FIG. 17, the beneficial effect of surface cooling is clearly indicated and even greater deep heat to 9 centimeters is accomplished with the surface at physiologic temperatures. As shown in this chart, with surface cooling the skin is maintained at a fairly uniform temperature of below 20° C.; the subcutaneous tissue is at first cooled and then gradually rises to about 40° C. after 30 minutes, and the deep (9 centimeters) muscle heat gradually rises after 10 minutes to about 41°, 42° C.; the deep muscle temperature recedes slightly and then increases to about 42° to 43° C. after 30 minutes. This chart indicates that surface cooling and deep heating is applicable to deep musclo-skeletal disease states.

The chart of FIG. 18 discloses heating and cooling effects of an electrode means of this invention during treatment of a 15×15×15 centimeter human chest muscle tumor and overlying skin and subcutaneou tissue, with pretreatment ambient temperatures of 41° C. Prior to treatment with radio frequency waves the body was subjected to cooling for about 10 minutes during which the temperature of the skin was reduced to about 17° C. and temperature of the subcutaneous tissue reduced to about 32° C. The temperature of the tumor during this period remained at about 41° C. Upon initiation of treatment of energizing the electrode means of this invention, the chart indicates for a period of 35 minutes of exposure to electromagnetic energy, the temperature of the skin increased slightly to 20° C. and that of the subcutaneous tissue did not exceed 38° C., these temperatures being relatively low and physiologic temperatures. Meanwhile the human tumor was heated to greater than 45° C. for 30 minutes and as the chart indicates the tumor reached 63° C. at the end of 35 minutes of treatment. Such an effective degree of tumor heating with preservation of normal tissue at relatively low physiologic temperatures (less than 40° C.) has, to my knowledge, never been achieved.

In FIG. 6, a modification of the electrode means 12 is illustrated. The central portion of FIG. 6 includes an electrode construction identical to that described in FIGS. 3 and 4, and wherein chamber 23 has a bottom wall 21, partition walls 24, a top wall 20 and edge walls 22; inlet and outlet fittings 26 and 27 are similarly provided and connected to suitable fluid conducting lines. Inlet fitting 26 may be connected to a fluid source 26a. To provide surface cooling peripherally beyond the edge of the emitting wall 21 and emitting surface 21a thereof, a peripheral jacket means 30 of plastic non-radio frequency emitting material may encircle or surround the periphery of the electrode means 12. Cooling jacket 30 may be secured to the edge walls 22 at 31 in any suitable manner as by adhesive bonding. Jacket 30 is provided with an inlet fitting 32 and an outlet fitting 33, inlet fitting 32 may be connected to a source 26a of cooling fluid similar to the source for electrode means 12. It will be understood that the cooling fluid circulated through the continuous passageway 34 of jacket 30 may be the same as that circulated through electrode means 21 or may be from a different source 36a to provide independent cooling fluid of selected temperature, higher or cooler than the cooling fluid in electrode means 12. The selection of the cooling fluid temperature will be dictated by the body under treatment. The jacket 30 may be comprised of plastic or other suitable non-metallic material and is not designed to emit radio frequency waves.

In FIG. 8, another modification of the electrode means of this invention is generally indicated at 40. Electrode means 40 comprises a top wall 41, side walls 42 and a bottom wall 43 made of a pliant, flexible fluid-impervious metallized and conductive material. The walls 41, 42 and 43 define a chamber 44, top wall 41 having an inlet fitting 45 and an outlet fitting 46. Fittings 45 and 46 may communicate with suitable conduits or pipe for conducting a cooling fluid into and through chamber 44 in a manner similar to that described in the prior modification.

Electrode means 40 may be provided with a suitable "O" ring seal 47 between the bottom edge of wall 42 and an annular shoulder surface 48 provided on an annular wall 49 having a cylindrical portion 49a slidably received internally of wall 42. Edge margins of flexible wall 43 overly seal 47. A pressure tight seal is made between surface 48, seal 47, margins of wall 43, and wall 42 and may be secured by suitable screw bolts 50'.

The flexibility and pliancy of bottom wall 43 permits external surface 51 thereof to closely conform to virtually any three-dimensional surface configuration on a body. The introduction of cooling fluid into chamber 44 imposes an internal outwardly directed pressure on the bottom wall 43 which causes the bottom wall 43 to closely conform and cling to the surface against which it is directly contacted. Since the flexible wall 43 serves as the electrode for transmitting shortwave frequencies, the amount of surface area of wall 51 in contact with the skin surface will depend upon the internal fluid pressure in chamber 44 and the pressure imposed upon the electrode means in the form of a securing strap in order to hold the electrode means in proper location and position on the body member. Since the contact area is one of the factors in determining the amount of dosage and the time of treatment, it may be desirable to identify surface area by suitable reference markings on the exterior surface of the flexible wall 43.

It will be understood that the electrode means 40 will be connected to the impedance matching circuit and power source as schematically illustrated in FIG. 1 and may be applied to opposite sides of a body member as described in the prior embodiment of this invention or singly as in the case of microwave application. It may be desirable to provide partition means in chamber 44 to provide a circulation path for the cooling fluid to uniformly cool the bottom wall 43. Since bottom wall 43 is flexible, such partitions may be unsecured with respect to the bottom wall to permit the bottom wall to adequately conform to this configuration of the skin surface against which it is directly contacted.

In FIG. 9 is a further modified electrode means to provide surface cooling beyond the edges of the emitting surface of an electrode constructed as electrode means 40, FIG. 8. In FIG. 9, the central part of electrode means 50 is substantially identical to the structure of electrode means 40 and is identified by reference numeral 40'. Electrode means 40' includes top wall 41', side walls 42', bottom wall 49', a chamber 44', and an emitting wall 43' having an emitting surface 51'. Inlet 45' and and outlet 46' is also provided.

Surrounding electrode means 40' is a flexible, pliant wall 53 of suitable dielectric material and having edge margins secured in pressure tight, sealed relation between an annular flange and a securement ring 55 retained by screw bolts 56. Annular flange 54 is carried by a cylindrical wall 57 within which is received the wall 42' of electrode means 40'. Screw bolts 58 secure the flange 54 and cylindrical wall 57 to the inner electrode means 40'. Flange 54 is provided with an inlet fitting 59 and an outlet fitting 60 for circulation of cooling fluid through said inlet and outlet and through the outer peripheral chamber 61 defined by the flange 54, outer flexible wall 53 and inner emitting wall 43'. As in the prior example of FIGS. 6 and 7, the chamber 61 provides surface cooling beyond the peripheral edges of the emitting electrode surfaces. The cooling fluid circulated may be from a similar or different source and may have a temperature the same as or different from the cooling fluid circulated through chamber 44'. The flexible dielectric wall 53 is adapted to directly contact skin surface and is held in pressure contact therewith by the pressure of the fluid circulating in outer chamber 61 and inner chamber 44'. It is understood that electrode means 50 may be secured by a suitable strap or other means to the body portion which is being treated.

FIGS. 10 and 11 show still another modification of the electrode means of this invention wherein the means defining the chamber for circulating cooling fluid as well as the electrode emitting surface are flexible so that the entire electrode means may conform to body contour. In this example of the invention, the emitting surface 71 of the electrode means generally indicated at 72 may comprise a flexible metallized plastic cloth to provide emitting surface 71; the metallized cloth having an electrical contact with a radio frequency terminal post 73 for transmission of electromagnetic energy to the cloth.

Cooling chamber means 74 is provided by a flexible tubing of suitable size and internal diameter wound in spiral fashion about the post 73 and outwardly therefrom to cover the area of the metallized material 75 providing the emitting surface 71. The tubing may be suitably connected to a source of cooling fluid.

It will be apparent that in this construction of an electrode means embodying this invention extreme flexibility of both the emitting surface and the cooling means is provided for readily adapting and conforming the emitting surface to the surface configuration of a body which is being treated. Securement means for the electrode means 72 may include a strap or other suitable holding means for maintaining the emitting surface 71 in direct contact with the body portion being treated.

In a modification of the electrode means 72 shown in FIG. 14, the electrode means generally indicated at 80, FIG. 14, differs from the electrode means 72 in that the flexible material is a flexible metal screen 81 providing an emitting surface. In this embodiment, the electrode emitting screen 81 is covered by a thin, mylar or dielectric sheet 82 to prevent imprint of the wire screen on the skin surface. Such imprinting of the screen is indicative of non-uniform contact of the emitting surface with the skin surface with the result that undesired non-uniform heating of the skin may occur upon transmission of electromagnetic energy from the emitting screen to the skin and subcutaneous tissue.

It will be understood that a thin dielectric sheet may be placed beneath the emitting surface 71 of electrode means 72, if desired. The electrode means 80 is adapted to be mounted on a body portion in the same manner as electrode means 72 as described above.

In FIGS. 12 and 13, a further modification of the electrode means 72 is shown wherein additional cooling tubing 74 is wound around the inner coils of tubing so as to extend the cooling area of the cooling fluid beyond the edges of the emitting surface. The construction of the electrode means 90 is similar to electrode means 72 and includes the flexible emitting surface 71' an RF terminal post 73' and tubing 74' for circulation of cooling fluid in a flexible spiral path around the flexible metallized material 75. In this modification, two extra turns of the tubing are made as indicated at 91 to provide the cooling of tissue peripherally beyond the edge of the emitting surface 71'.

Electrode means 90 may be secured to a body portion by a suitable strap, belt or other means as previously described and the cooling fluid circulated through the tubing may be of any preselected temperature as previously described.

In FIG. 5 still another embodiment of the invention is illustrated wherein a separate fluid tight bag 95 of suitable flexible material may be filled with an electrolyte solution 96 such as salt water. Bag 95 may be placed upon skin surface 15 of a body and will readily conform to the surface of the body. On top of the bag 95 may be placed an electrode means of this invention, in this example, an electrode means 12 as shown in FIGS. 3 and 4. The emitting surface of the bottom wall 21 of the electrode 12 transmits electromagnetic energy into the electrolyte solution 96 which conducts and transmits the electromagnetic energy to the bottom wall 97 of the bag which is pressed against the skin surface 15 and which permits the radio frequency waves emitted by the electrode means 12 to be directed into the body portion. It will be apparent that an electrode means 12 as described will readily adapt itself to any surface configuration because of the presence of the bag 95 which will not deter or affect the transmission of the electromagnetic waves because of the electrolyte solution carried thereby.

In FIG. 15 still another embodiment of the invention is illustrated wherein a separate flexible pliant bag 98 of suitable material is provided with an inlet 99 and an outlet 100 for circulation of cooling fluid of selected temperature through the bag. An electrode emitter 101 is made of suitable flexible material such as a wire screen, thin metal sheet, or metallized plastic as previously described and is contained within the bag in direct interfacial contact with the lower bag wall 103 which is positionable against a skin surface. The electrode emitter 101 is suitably connected to an electromagnetic energy source as heretofore described through a wire or terminal 102 which extends through a wall of the bag in suitably sealed relationship therewith. The direct interfacial contact between the emitter 101 and the lower bag wall 103 is provided by a flexible porous material 104 of suitable shape such as sponge rubber or flexible fiberglass fibers contained within the bag and between the emitter 101 and the upper bag wall 106. When the electrode is secured to a body by broad dielectric straps 105 the pressure of the straps against the bag is transmitted through the porous flexible material 104 to provide pressure and direct interfacial contact between the electrode emitter surface and lower bag wall 103 and the surface of the body. This embodiment provides still another example of electrode flexibility which permits the emitter and the bag wall to closely conform to body contours.

It will be understood that the several electrode means described above may be employed in pairs for the creation of an electromagnetic field between two opposed electrode means operating at shortwave frequencies. In some treatments it may be desirable to employ microwave frequencies wherein a single electrode means of the type described above may be positioned on the body of a patient and microwave energy transmitted to the body for the deep heating of tumorous or musclo-skeletal tissue.

FIG. 2 illustrates a single electrode means 12 placed upon the thigh of a leg 11 of the body of a patient and having a suitable connection 108 to an impedance matching circuit and power source adapted to provide microwave energy to the electrode means 12. Electrode means 12 has a cooling chamber as previously described.

It will be noted that in this adaptation of an electrode means for transmission of microwaves to a body, the emitting surface is in direct contact or in close proximity to the skin surface of the body of the patient. The cooling provided by the electrode means of this invention facilitates the use of microwave energy under such conditions.

The electrode means of this invention thus provides regulation and control of superficial heating of normal living tissue while permitting the application of electromagnetic radio frequency heating at relatively great depths of tumor bearing or otherwise diseased tissue in a body. Cooling of the superficial tissue is controlled by the regulation of the cooling fluid in terms of rate of flow and temperature of fluid circulated so that living tissue which is subjected to heating by the shortwaves in the electromagnetic field between the two electrode means or by microwaves under a single electrode can be kept at a suitable selected temperature which will not damage the tissue. The electrode means and modified electrode means also include provision for circulating coolant beyond the edge of the electrode emitting surface to provide suitable selected temperature of tissue adjacent to the electrode otherwise subjected to heating by the near electromagnetic field.

Modified electrode means provide for conformity to body contour. Thus, the possibility of burning the surface skin or portions of the subcutaneous tissue by the radio frequency waves is virtually eliminated under proper controlled conditions.

It will be understood that various modifications and changes may be made in the electrode means of this invention which come within the spirit of the invention and all such changes and modifications coming within the scope of the appended claims are embraced thereby.

I claim:

1. In an apparatus for localized application of heat to a body having an internal body portion of different characteristics than surrounding body portions and including a radio frequency wave source for emitting electromagnetic waves such as short and microwave frequencies, and having means for matching impedance of the wave source and impedance of the body portion in the field of said electromagnetic waves, the provision of:

an electrode means operatively connected to said radio frequency wave source and impedance matching means, said electrode means being adapted to be externally positioned with respect to said body portions, said electrode means having a wall providing an electrode emitting surface adapted to be positionable in close proximity with external surfaces of said surrounding body portions;

and means for cooling the surrounding body portions by cooling said wall of said electrode means while heating said internal body portion by said emitted waves.

2. An apparatus as claimed in claim 1 wherein said emitting surface of said electrode means is adapted to be in direct interfacial contact with said body portions and has a configuration to correspond with the surface on said body over a predetermined area.

3. An apparatus as claimed in claim 1 wherein said cooling means includes:

means for circulating a cooling fluid within said electrode means, said cooling fluid having circulating contact with the interior face of said wall providing said emitting surface on said electrode means.

4. An apparatus as claimed in claim 3 including means for circulating cooling fluid beyond and peripheral to said emitting surface.

5. An apparatus as claimed in claim 1 wherein said cooling means includes:

a chamber within said electrode means provided with an inlet and an outlet;

cooling fluid circulating means in communication with said inlet and outlet whereby said cooling fluid passes into and out of said chamber in heat transfer relationship with said emitting surface adapted to be in direct contact with said body;

and baffle partitions in said chamber enhancing uniform cooling of said wall.

6. An apparatus as stated in claim 1 wherein said emitting surface adapted to be in contact with said body surface is flexible to directly contact and correspond to multidimensional configurations of the body surface to assure direct cooling contact over a predetermined body surface area.

7. In an apparatus as claimed in claim 1 wherein said emitting surface on said electrode means for direct contact with said body surface is provided by a flexible metallized material sheet conformable under pressure to the body surface for direct contact therewith over a preselected area.

8. In an apparatus as claimed in claim 7 wherein said cooling means provides fluid pressure for conforming the flexible sheet to the body surface.

9. An electrode for transmitting radio frequency electromagnetic energy and adapted to be connected to a power source, comprising:

an electrode body structure having a chamber with a wall thereof having an electrode emitting surface adapted to be placed in close heat exchange proximity to a surface of a body being treated;

means for connecting the electrode emitting surface to said power source;

and means for cooling said emitting surface and adjacent body surfaces including means for circulating cooling fluid through said chamber in heat transfer relation to said wall, emitting surface and body surfaces.

10. An electrode as claimed in claim 9 wherein said emitting surface is flexible and conformable to said body surface.

11. An electrode as claimed in claim 9 wherein said emitting surface comprises a flexible, metallized, conductive sheet of material adapted to transmit radio frequencies and to transfer heat for maintaining adjacent contacted portions of said body relatively cool.

12. An electrode as claimed in claim 9 including means for circulating cooling fluid beyond and adjacent to peripheral edges of said emitting surface.

13. A method of localized application of heat to a relatively deep internal body portion while maintaining surrounding body and surface portions relatively cool comprising the steps of:

positioning a wall of a chamber having an electromagnetic radio frequency energy emitting surface of selected area thereon in close heat transfer proximity to external surfaces of corresponding area of said surrounding body and surface portions;

applying radio frequency energy to the emitting surface;

and cooling said emitting surface and said surrounding body portions by flow of cooling liquid along said wall internally of said chamber.

14. In a method as stated in claim 13 including the step of:

cooling body portions extending peripherally beyond said emitting surface.

15. In an apparatus for localized application of heat to a body having an internal body portion of different characteristics than surrounding body portions and including a radio frequency wave source for emitting electromagnetic waves such as short and microwave frequencies, and having means for matching impedance of the wave source and impedance of the body portion in the field of said electromagnetic waves, the provision of:

an electrode means operatively connected to said radio frequency wave source and impedance matching means, said electrode means being externally positionable with respect to said body portions, said electrode means having a wall providing an emitting surface positionable in close proximity with external surfaces of said surrounding body portions;

and means for cooling the surrounding body portions adjacent to said electrode means while heating said internal body portion;

said cooling means including means for circulating a cooling fluid within said electrode means, said cooling fluid having circulating contact with the interior face of said wall providing said emitting surface on said electrode means, said cooling means including means for circulating cooling fluid beyond and peripheral to said emitting surface, and means for independently varying temperature of said cooling fluid within said electrode means and of said cooling fluid peripheral to said emitting surface.

16. In an apparatus for treatment of internal tissues of a body by causing deep penetration of heat by utilizing a radio frequency wave source for emitting electromagnetic waves such as short and microwave frequencies, said internal tissue of a body having a characteristic different than surrounding body tissue, the provision of:

an electrode means adapted to be positioned on one or both sides of said body;

said electrode means including walls defining a chamber, one of said walls providing an electrode emitting surface;

inlet and outlet means to said chamber;

means electrically connecting said one wall to said radio frequency wave source;

said one wall providing said emitting surface being adapted to be placed in intimate or close proximity contact with the exterior skin of said body for heat transfer relation and for control of the electromagnetic field, means for circulating cooling fluid through said inlet and outlet means of said chamber and through said chamber in heat transfer relation with said wall providing said emitting surface, said cooling fluid serving to maintain said body surface and body tissue portions adjacent thereto relatively cool as compared to the body tissue being treated by radio frequency emissions from said emitting surface.

* * * * *